United States Patent [19]

Franklin

[11] Patent Number: 4,912,265

[45] Date of Patent: Mar. 27, 1990

[54] PHASE TRANSFER CATALYZED PROCESS FOR BOROHYDRIDE REDUCTIONS OF CARBONYL COMPOUNDS

[75] Inventor: Ralph Franklin, Naperville, Ill.

[73] Assignee: Akzo America Inc., New York, N.Y.

[21] Appl. No.: 237,345

[22] Filed: Aug. 26, 1988

[51] Int. Cl.[4] .................. C07C 29/14; C07C 27/04
[52] U.S. Cl. .................... 568/862; 568/814; 568/844; 568/861; 568/863; 568/864; 568/880
[58] Field of Search .............. 568/814, 844, 861, 864, 568/862, 863, 880

[56] References Cited

U.S. PATENT DOCUMENTS

| | | | |
|---|---|---|---|
| 2,683,721 | 7/1954 | Schlesinger | 568/814 |
| 2,874,165 | 2/1959 | Brown | 568/814 |
| 3,992,432 | 11/1976 | Napier et al. | 260/465.1 |
| 4,107,099 | 8/1978 | Hedge | 568/862 |

FOREIGN PATENT DOCUMENTS

| | | | |
|---|---|---|---|
| 0161927 | 8/1985 | Japan | 568/816 |
| 2155464 | 9/1985 | United Kingdom | 568/814 |

OTHER PUBLICATIONS

*Phase Transfer Catalysis*, E. V. Dehmlow & S. S. Dehmlow, Verlag Chemie, 1980, Chapter 3, pp. 52-55.
*Phase Transfer Catalysis-Principles & Techniques*, C. M. Starke & C. Liotta, Academic Press, 1978, pp. 60 & 64.
"N-Dodecyl-N-Methylephedrinium Bromide: A Specific Catalyst for the Borohydride Reduction of Carbonyl Compounds Under Phase Transfer Conditions", Stefano Colonna and Roberto Fornasier, *Synthesis*, Aug., 1975, p. 531.
"Asymmetric Induction in the Borohydride Reduction of Carbonyl Compounds by Means of a Chiral Phase Transfer Catalyst", Jose Balcells, Stefano Colonna, Roberto Fornasier, *Synthesis*, Apr., 1976, p. 266.
"Asymmetric Induction in The Borohydride Reduction of Carbonyl Compounds by Means of Chiral Phase-Transfer Catalysts, Part 2", Stefano Colonna & Robert Fornasier, *J.C.S. Perkin Trans I,* 1978, p. 371.
"Asymmetric Reduction of Ketones by Phase Transfer Catalysis", J. P. Massee & E. R. Parayre, *J.C.S. Chem. Comm.,* 1976, p. 438.

*Primary Examiner*—Werren B. Lone
*Attorney, Agent, or Firm*—David H. Vickrey; Louis A. Morris

[57] ABSTRACT

A process for the reduction of carbonyl compounds by an alkali or alkaline-earth metal borohydride in the presence of a phase transfer catalyst which is an N-benzyl-N,N-bis (2-hydroxyethyl)cocoammonium halide.

7 Claims, 4 Drawing Sheets

PHASE TRANSFER CATALYZED PROCESS FOR BOROHYDRIDE REDUCTIONS OF CARBONYL COMPOUNDS

This invention pertains to phase transfer catalyzed reduction of carbonyl compounds by an alkali or alkaline-earth borohydride. In particular, it relates to the use of an N-benzyl-N,N-bis(2-hydroxyethyl)cocoammonium halide as the phase transfer catalyst.

BACKGROUND OF THE INVENTION

Phase transfer catalysis ("PTC") is a synthesis method which allows the use of relatively simple two-phase reaction systems in the place of solvent systems which may be toxic and/or expensive.

In fundamental terms, PTC employs a phase transfer catalyst which facilitates the transfer of a reactive species from the first phase, normally aqueous, into the second phase, normally organic, where the desired reaction can take place. For example, a phase transfer catalyst may be used to transport a cyanide ion from an aqueous solution of sodium cyanide to an organic solution of an alkyl halide where the cyanide ion reacts with the alkyl halide to form alkyl nitrile.

PTC is known to be a valuable technique for accomplishing a wide range of reactions. For example, PTC is known to facilitate nucleophilic substitution reactions, hydroxide transfer, esterification, oxidation and reduction. Specifically, U.S. Pat. No. 3,992,432 claims the use of certain quaternary salts as phase transfer catalysts to effectuate reactions such as displacement reactions (for example the earlier described preparation of alkyl nitrile), oxidation of organic compounds with inorganic oxidizing agents, ester saponification and the conversion of carbonyl compounds to alcohols. The quaternary salts for use as phase transfer catalysts taught and claimed in U.S. Pat. No. 3,992,432 are of the general formula $(R_1R_2R_3R_4M)^+X^-$ wherein M is nitrogen, arsenic, phosphorus, antimony or bismuth; X is a halide or hydroxy ion; and $R_1$, $R_2$, $R_3$ and $R_4$ are monovalent hydrocarbon radicals having a total sum of 18 to 70 carbon atoms, one of which may be further substituted by a quaternary group so the salt is represented by $R_1[(R_2R_3R_4M)^+X^-]_2$. In Example 41 of U.S. Pat. No. 3,992,432, 2-octanone is reduced to 2-octanol by sodium borohydride in the presence of the phase transfer catalyst tricaprylylmethyl ammonium chloride.

Reduction of the aromatic compound $C_6H_5(C:OX)$ (where X is halo and the benzene ring may be optionally substituted) to $C_6H_5(CH_2OH)$ with an alkali or alkaline-earth metal borohydride in the presence of a phase transfer catalyst (which may be a quaternary ammonium compound) is known from GB 2 155 464 A.

Also, the article "N-Dodecyl-N-methylephedrinium Bromide: a Specific Catalyst for the Borohydride Reduction of Carbonyl Compounds under Phase-Transfer Conditions" (Stefano Colonna and Roberto Fornasier, *Synthesis*, August 1975, pages 531-2) compares the performance of five phase transfer catalysts in the reduction of 2-octanone to 2-octanol with sodium borohydride. Among the five phase transfer catalysts reported by Colonna et al. are N-dodecyl-N-methylephedrinium bromide and bis[2-hydroxyethyl]-dodecylmethylammonium bromide (referred to in Colonna et al. as "bis[2-hydroxyethyl]-dodecylmethylaminium bromide"). Colonna et al. also suggest on page 532 the presence of a hydroxy group in the catalyst enhances the rate of reduction. In a separate article, (*Journal of the Chemical Society Perkin Trans I*, "Asymmetric Induction in the Borohydride Reduction of Carbonyl Compounds by Means of Chiral Phase-transfer Catalysts. Part 2.", 1978, pages 371-3). Colonna and Fornasier report that to achieve asymmetric induction in the borohydride reduction of carbonyl compounds under phase-transfer conditions, the hydroxy-group must be in the β position to the 'onium' function and the catalyst must be conformationally rigid.

The above-mentioned references do not disclose that N-benzyl-N,N-bis(2-hydroxyethyl)cocoammonium halides are superior phase-transfer catalysts in processes for reducing carbonyl compounds by an alkali or an alkaline-earth metal.

Surprisingly, it has been found that in the alkali or alkaline-metal earth borohydride reduction of carbonyl compounds use of an N-benzyl-N,N-bis(2-hydroxyethyl)cocoammonium halide as a phase transfer catalyst provides a more rapid reduction reaction when compared with known phase transfer catalysts. The process of the current invention is particularly useful in the reduction of ketones to the corresponding alcohols, such as the reduction of 2-octanone to 2-octanol.

SUMMARY OF THE INVENTION

Accordingly, the current invention is a process for conducting a reduction reaction in a two-phase reaction system, the process comprised of reducing carbonyl compounds by an alkali or an alkaline-earth metal borohydride in the presence of a phase transfer catalyst which is an N-benzyl-N,N-bis(2-hydroxyethyl)cocoammonium halide.

DETAILED DESCRIPTION OF THE INVENTION

Figure 1:
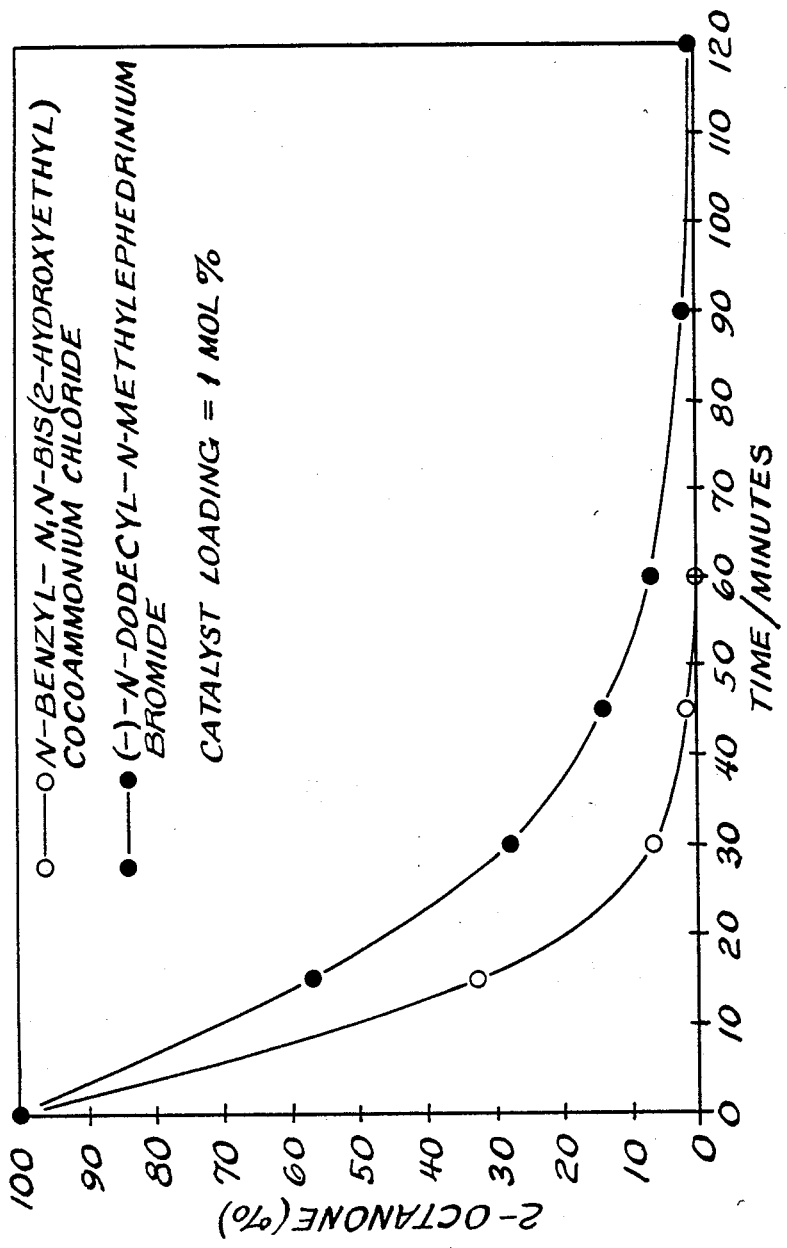
FIG. 1 is a plot of the reaction rate of the reduction of 2-octanone comparing use of the phase transfer catalysts N-benzyl-N,N-bis(2-hydroxyethyl)cocoammonium chloride and (−)-N-dodecyl-N-methylephedrinium bromide on an equimolar basis.

The current invention is a process for conducting a phase transfer catalyzed reduction reaction in a two-phase reaction system. The process is comprised of reducing a carbonyl compound by an alkali or alkaline-earth metal borohydride in the presence of an N-benzyl-N,N-bis(2-hydroxyethyl)cocoammonium halide as a phase transfer catalyst.

In the current phase transfer catalyzed synthesis process, an alkali or alkaline-earth metal borohydride is present in an aqueous first phase and a carbonyl compound is present in the organic second phase. To reduce the carbonyl compound, the borohydride must be transported from the aqueous first phase to the organic second phase by a phase transfer catalyst. It has been found that use of an N-benzyl-N,N-bis(2-hydroxyethyl)-cocoammonium halide as the phase transfer catalyst greatly facilitates reduction of carbonyl compounds.

Non-limiting example carbonyl compounds which may be reduced by the phase transfer process of the current invention include aliphatic ketones, such as methylethyl ketone, octanone and cyclohexanone; aryl ketones, such as benzophenone and substituted benzophenones; alkylaryl ketones, such as acetophenone and propiophenone; aliphatic aledehydes, such as butyraldehyde and octaldehyde; and aryl aldehydes, such as benzaldehyde and tolualdehyde. Mixtures of carbonyl compounds may also be reduced by the process of the current invention.

Any compound which will contribute a borohydride ion for reduction of the carbonyl compound may be used in the current process. Of particular utility are alkali and alkaline-earth metal borohydrides, such as sodium borohydride and potassium borohydride.

As demonstrated by the following non-limiting examples, N-benzyl-N,N-bis(2-hydroxyethyl)cocoammonium halides are surprisingly superior phase transfer catalysts when compared to known phase transfer catalysts in the reduction of carbonyl compounds. In particular, N-benzyl-N,N-bis(2-hydroxyethyl)cocoammonium chloride is a superior phase transfer catalyst for such reduction reactions.

EXAMPLE 1

Equimolar comparison of
N-benzyl-N,N-bis(2-hydroxyethyl)cocoammonium chloride and (—)-N-dodecyl-N-methylephedrinium bromide as phase transfer catalysts in reduction of 2-octanone to 2-octanol Two 250 ml flasks fitted with mechanical stirrer, condenser and thermometer were each charged with 2-octanone (6.44 g, 0.05 mol) and toluene (30 ml). As catalyst, N-benzyl-N,N-bis(2-hydroxyethyl)cocoammonium chloride (0.0005 mol), available from Akzo Chemicals Inc. under the product name Armak 1733 (75% active component solution), was added to the first flask and (—)-N-dodecyl-N-methylephedrinium bromide (0.0005 mol) available from Aldrich Chemical Co., was added to the second flask. Hexadecane (1.0 g) was added to each flask as an internal GLC standard. Potassium borohydride (1.63 g, 0.03 mol) was added to each reaction mixture along with 50 ml of water. At this point, stirring and timing were started. The stirrer speed setting was 600 rpm. Periodically, each stirrer was stopped and a sample of each organic phase taken for GLC analysis. These results are reported in FIG. 1.

The data reported in FIG. 1 amply demonstrate that, on a mole for mole basis, the new phase transfer catalyst N-benzyl-N,N-bis(2-hydroxyethyl)cocoammonium chloride surprisingly provides a more rapid reduction of 2-octanone to 2-octanol when compared to the phase transfer catalyst (—)-N-dodecyl-N-methylephedrinium bromide known from Colonna et al., *Synthesis*, August 1975 as discussed above.

EXAMPLE 2

Weight basis comparison of
N-benzyl-N,N-bis(2-hydroxyethyl)cocoammonium chloride and (—)-N-dodecyl-dimethylephedrinium bromide as phase transfer catalysts in reduction of 2-octanone to 2-octanol.

Figure 2:
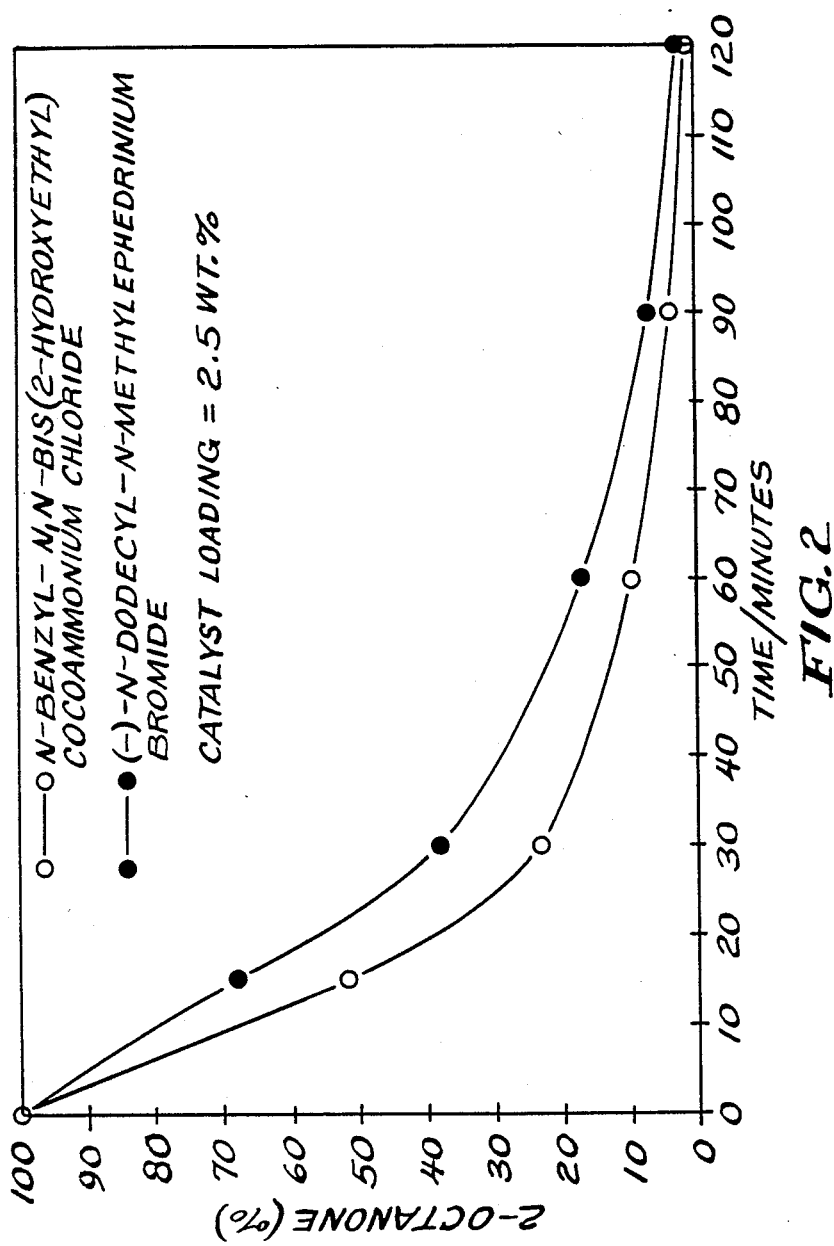
FIG. 2 is a plot of the reaction rate of the reduction of 2-octanone comparing use of the phase transfer catalysts N-benzyl-N,N-bis(2-hydroxyethyl)cocoammonium chloride and (−)-N-dodecyl-N-methylephedrinium bromide on a weight for weight basis.

The rate of reduction of 2-octanone to 2-octanol catalyzed by the new phase transfer catalyst N-benzyl-N,N-bis(2-hydroxyethyl)cocoammonium chloride was compared to the same reduction reaction catalyzed by the phase transfer catalyst (—)-N-dodecyl-N-methylephedrinium bromide known from Colonna et al., *Synthesis*, August 1975. A procedure substantially similar to that of Example 1 was employed except 0.16 g of each catalyst in their commercially available forms and concentrations were used in each reduction reaction. The results are reported in FIG. 2.

Placing the two catalysts on an equal weight basis puts the new catalyst N-benzyl-N,N-bis(2-hydroxyethyl)cocoammonium chloride at a disadvantage since its commercially available form is only 75% active. In spite of this disadvantage, the new N-benzyl-N,N-bis(2-hydroxyethyl)cocoammonium chloride surprisingly out performed the known (—)-N-dodecyl-N-methylephedrinium bromide.

EXAMPLE 3

Figure 3:
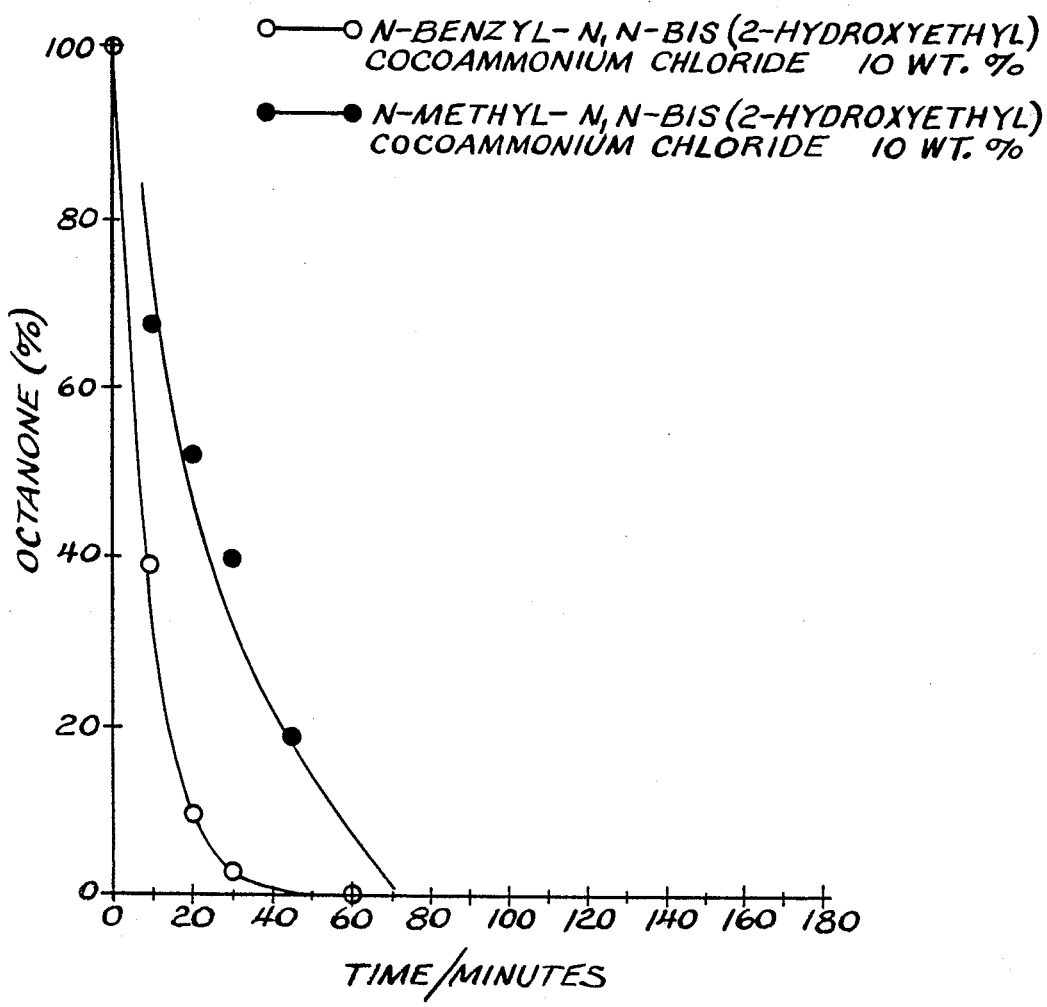
FIGS. 3 and 4 are plots of the reaction rate of the reduction of 2-octanone comparing use of the phase transfer catalysts N-benzyl-N,N-bis(2-hydroxyethyl)-cocoammonium chloride and N-methyl-N,N-bis(2-hydroxyethyl)cocoammonium chloride on weight for weight bases.
Figure 4:
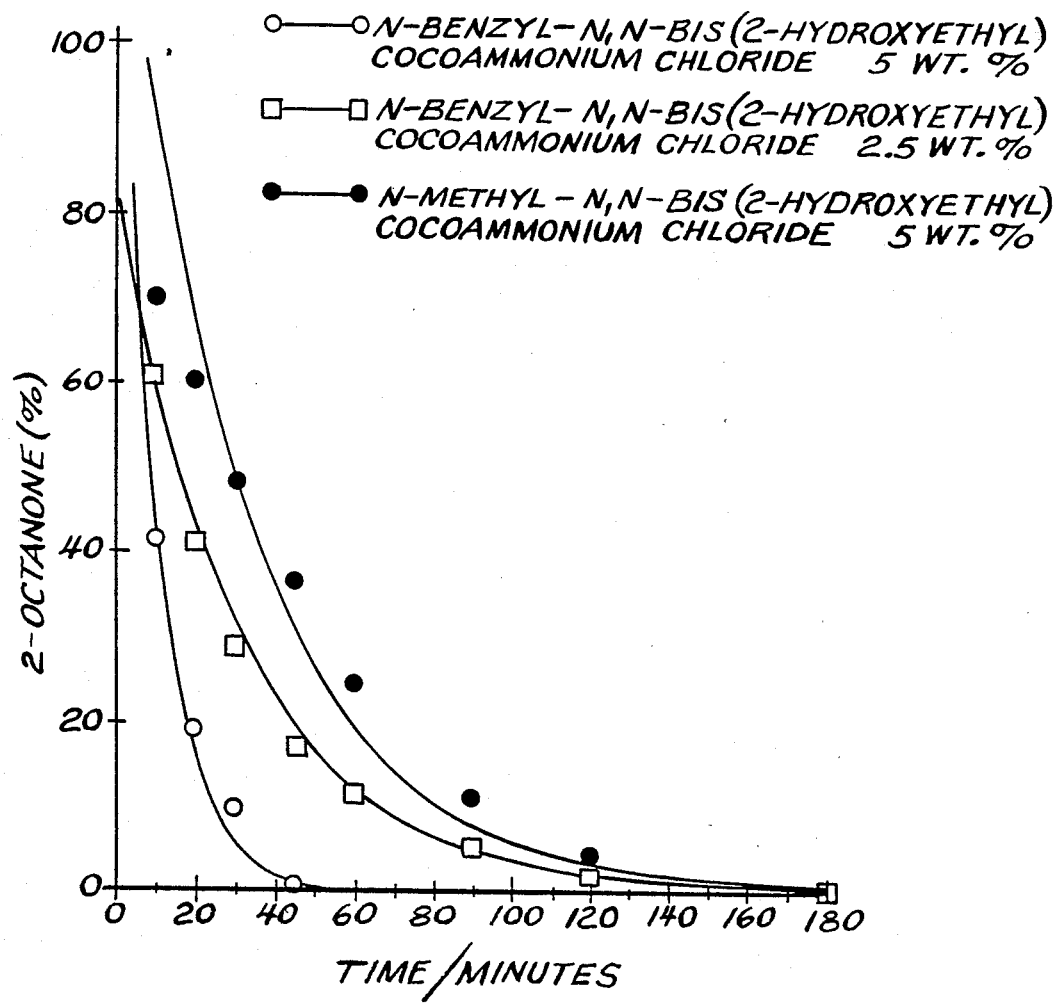

Weight basis comparison of
N-benzyl-N,N-bis(2-hydroxyethyl)cocoammonium chloride and
N-methyl-N,N-bis(2-hydroxyethyl)cocoammonium chloride as phase transfer catalysts in reduction of 2-octanone to 2-octanol The rate of reduction of 2-octanone to 2-octanol catalyzed by the phase transfer catalyst of the current invention N-benzyl-N,N-bis(2-hydroxyethyl)cocoammonium chloride was compared to the same reduction reaction catalyzed by the known phase transfer catalyst N-methyl-N,N-bis(2-hydroxyethyl)cocoammonium chloride, available from Akzo Chemicals Inc. under the product name Ethoquad C12. Procedures substantially similar to those of Example 1 were employed except the two catalysts were compared on a 10 wt. % basis and a 5 wt. % basis. Also, a reduction reaction was carried out using 2.5 wt. % N-benzyl-N,N-bis(2-hydroxyethyl)-cocoammonium chloride with no corresponding reduction reaction using 2.5 wt. % N-methyl-N,N-bis(2-hydroxyethyl)cocoammonium chloride. The results are reported in FIG. 3 and FIG. 4. The phase transfer catalyst of the current invention out-performed N-methyl-N,N-bis(2-hydroxyethyl)cocoammonium chloride even though N-benzyl-n,N-bis(2-hydroxyethyl)cocoammonium chloride is disadvantaged in a weight for weight comparison because it is of greater molecular weight.

EXAMPLE 4

Comparison of
N-benzyl-N,N-bis(2-hydroxyethyl)cocoammonium chloride and (—)-N-dodecyl-N-methylephedrinium bromide as phase transfer catalysts in reduction of acetophenone to sec-phenethyl alcohol In a qualitative experiment, the comparison was made of the two above-named catalysts in the phase-transfer reduction of acetophenone to sec-phenethyl alcohol. The reduction reactions were carried out using 2 mol % of each catalyst relative to the acetophenone and employing procedures substantially similar to those of Example 1. The reaction catalyzed with N-benzyl-N,N-bis(2-hydroxyethyl)cocoammonium chloride finished after about 100 minutes while the reaction catalyzed with (—)-N-dodecyl-N-methylephedrinium bromide required about 150 minutes. This demonstrates that the superior catalytic activity of N-benzyl-N,N-bis(2- hydroxyethyl)cocoammonium chloride is not limited to aliphatic carbonyl compounds.

I claim:

1. A process for conducting a reduction reaction in a two-phase reaction system, said process comprised of reducing a carbonyl compound to the corresponding alcohol by an alkali or alkaline-earth metal borohydride in the presence of a phase transfer catalyst which is an N-benzyl-N,N-bis(2-hydroxyethyl)cocoammonium halide, said carbonyl compound selected from the group consisting of aliphatic ketones, aryl ketones, alkylaryl ketones, aliphatic aldehydes, aryl aldehydes and mixtures thereof.

2. The process of claim 1 wherein the phase transfer catalyst is N-benzyl-N,N-bis(2-hydroxyethyl)cocoammonium chloride.

3. The process of claim 1 wherein the alkali or alkaline-earth metal borohydride is selected from the group consisting of potassium borohydride and sodium borohydride.

4. The process of claim 1 wherein the carbonyl compound is an aliphatic ketone.

5. The process of claim 4 wherein the aliphatic ketone is 2-octanone.

6. The process of claim 1 wherein the carbonyl compound is an aryl ketone.

7. The process of claim 6 wherein the aryl ketone is acetophenone.

* * * * *